United States Patent [19]

Mei

[11] Patent Number: 5,617,603
[45] Date of Patent: Apr. 8, 1997

[54] BRUSH HEAD ASSEMBLY OF AN ELECTRIC TOOTHBRUSH

[76] Inventor: Tzeng J. N. Mei, No. 1, Kuo-Chi Rd., Hsin-Shin Village, Tainan Hsiang, Taiwan

[21] Appl. No.: 681,382

[22] Filed: Jul. 23, 1996

[51] Int. Cl.$^6$ ............................................. A61C 17/34
[52] U.S. Cl. ................................... 15/22.1; 15/22.4
[58] Field of Search ............................. 15/22.1, 22.2, 15/22.4

[56] References Cited

U.S. PATENT DOCUMENTS

| | | | |
|---|---|---|---|
| 4,545,087 | 10/1985 | Naham | 15/22.1 |
| 5,020,179 | 6/1991 | Scherer | 15/22.1 |
| 5,504,959 | 4/1996 | Yakawa et al. | 15/22.1 |
| 5,524,312 | 6/1996 | Tan et al. | 15/22.1 |

*Primary Examiner*—Gary K. Graham
*Attorney, Agent, or Firm*—Morton J. Rosenberg; David I. Klein

[57] ABSTRACT

The present invention provides a staggered swing brush head assembly of an electric toothbrush. There are two swing bodies adjoin in the head part of the toothbrush by a swing bar. They can wobble to the opposite direction as the rear swing body is driven to swing by an eccentric cam of a drive rod. By this means the vibration force of the electric toothbrush can be eliminated to the less, and the action of the brush hair is in accord with the correct method of cleaning tooth. On the other hand, the rotating drive rod with the threaded blade drives the water and the powder infiltrating into the shell trunks out through the slots under the centrifugal effect.

1 Claim, 4 Drawing Sheets

BRUSH HEAD ASSEMBLY OF AN ELECTRIC TOOTHBRUSH

BACKGROUND OF THE INVENTION

The present invention relates to an electric toothbrush, and more particularly to a staggered swing toothbrush that employs the brush units swinging staggeringly and harmonically to minimizes vibration as swinging, and a drive rod driven the brush units to swing, to rotate and to displace water drips or tooth powder.

In accordance with the previous electric toothbrush design, the moving direction of the brush can be classified as two categories: circumvolution and shuttling. Wherein the electric revolving toothbrush drives the brush in a rotary motion which drives the hair of brush in a circular rotation. But the correct way of brushing teeth, according to dentist, is to reciprocate along the space between the teeth. Whereas the electric swaying toothbrush is to drive the brush to sway in a certain angle by means of a lug of a shuttling flexible rod inserting in the beveled slot on the bottom portion of the brush unit. So the whole brush unit sways in one direction, synchronously, it will affect the balance of the brush unit in swaying. And for the convenience of stretching into the mouth, the trunk of the head unit of the toothbrush is designed to have a long and thin portion, therefore the brush unit: swaying in an unbalance state causing the toothbrush to vibrate which makes an unconfortable feeling to the palm holding the handle of the toothbrush, further affecting the cleaning the teeth.

In addition, most of the conventional electric toothbrushes do not have the device to drain water out and to clean the foreign objects which will generate filth to derive germ. The powder contained in the toothpaste along with the water drips infiltrate in brush body through the interval between the motion parts will block the internal parts working functionally and further to decrease the service life of the electric toothbrush.

SUMMARY OF THE INVENTION

A main object of the present invention is to provide a staggered swing toothbrush which swings harmonically and decreases vibration during cleaning teeth. A further object of the present invention is to provide an improved electric toothbrush which can displace water and foreign objects shell trunks drive out.

DESCRIPTION OF THE PREFERRED EMBODIMENT

Figure 1:
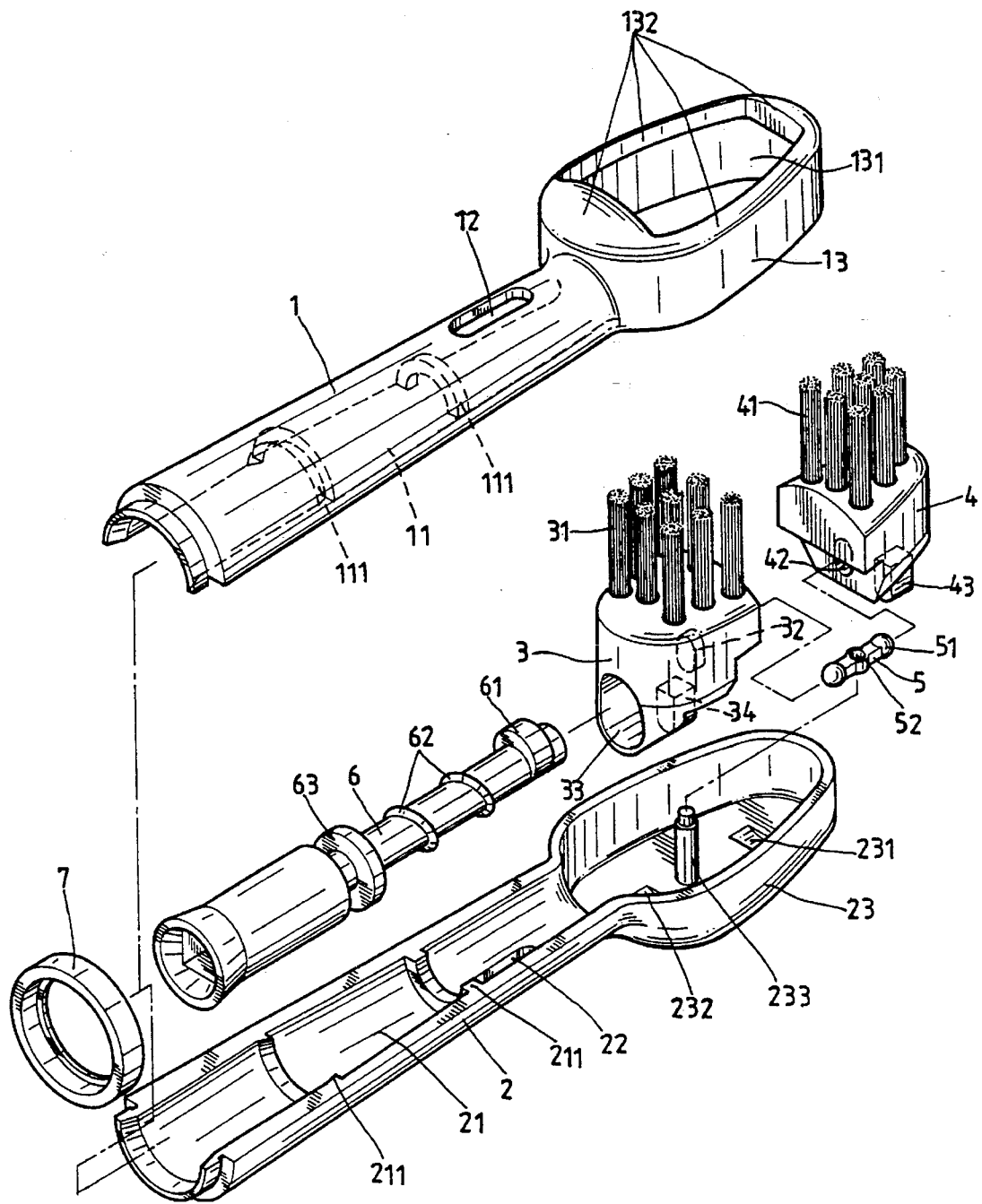
FIG. 1 is an exploded view of an electric toothbrush of the present invention.

Firstly referring to FIG. 1, the present invention comprises an upper and a lower shell trunks 1 and 2, two swing bodies 3 and 4 with one at the front and the other at the rear portions arranged tandem in the head part, a swing bar 5 located between the two swing bodies 3 and 4, and a drive rod 6. The upper shell trunk 1 and the low shell trunk 2 comprise a relative recesses 11 and 21 with respective flanges 111 and 211 for receiving and locating the drive rod 6 therein. A pair of opposite slots 12 and 22 are formed on the shell trunks 1, 2, respectively. A pair of head portions 13 and 23 are formed at the front end of the upper and the lower shell trunks 1 and 2, respectively, in which the head portion 13 of the upper shell trunk 1 has an opening 131 with a curved blocking rim 132 extending along the flange, and in which the lower shell trunk 2 has a pin 233 extending from the inner center portion, upwardly, and two concave grooves 231 and 232 located at the front and the rear portions individually. Upon the upper shell trunk 1 and the lower shell trunk 2 are sealed together, a pocket is defined by the two recesse 11 and 21.

The swing bodies 3 and 4 are a couple of adjoining tandem blocks corresponding in sizes to the head portions 13 and 23 of the shell trunks 1 and 2. The top surfaces of the two swing bodies 3 and 4 are curved and embedded with brush hair 31 and 41 separately, and a pair of recesses 32 and 42 on the adjoining interface of each swing body. The rear swing body 3 has an ellipsoid-shaped bottom at the rear bottom end having an oval blind hole 33 therethrough and a convex lug 34 at the front bottom end which corresponds to a convex lug 43 formed at the rear bottom end of the front swing body 4. The swing bar 5 has a longitudinal body with two ball ends 51 at respective end portions, and a socket 52 at the center portion of the bar. The drive rod 6 is a hollow shaft rod having a cam 61 at the front end, a helical blade 62 winding the cam 61, and a collar 63 at the rear end of the blade 62.

Figure 2:
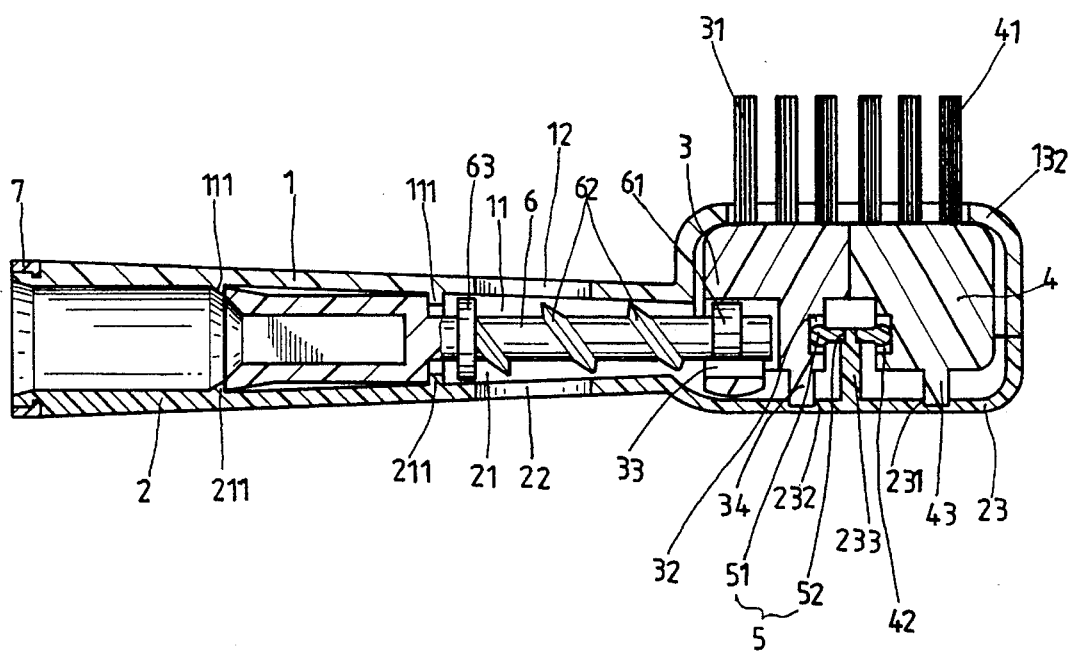
FIG. 2 is a side cross-section view of the present invention.

In combining, as shown in FIG. 2, first, place the swing bar 5 into the low shell trunk 2 with the socket 52 sleeved on the pin 233. Then place the swing bodies 3 and 4 into the lower shell trunk 2 with the two ball ends 51 inserted into the recesses 32 and 42, respectively, and the convex lugs 43 and 34 at the bottom sides of the swing bodies 3 and 4 embed into the two concave grooves 231 and 232 at the bottom of the lower shell trunk 2. Next, place the drive rod 6 into the pocket 21 of the lower shell trunks 2 with the front end extending into the head portions 13 and 23 and the cam 61 inserted into the oval blind hole 33 of the rear swing body 3. Last, cover the upper shell trunk 1 on the lower shell trunk 2 with the blocking rims 132 touching against each other preventing the swing bodies 3 and 4 from reciprocating as working, and secure the shell trunks together by means of heat fuse welding or other appropriate method, and reinforce with a retaining ring 7.

Figure 3:
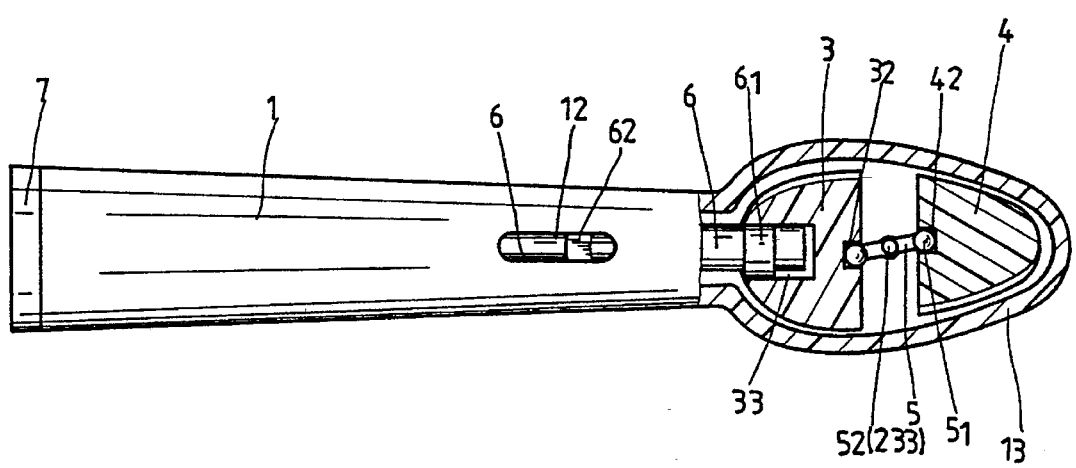
FIG. 3 is a top view showing the operation of the present invention.
Figure 4:
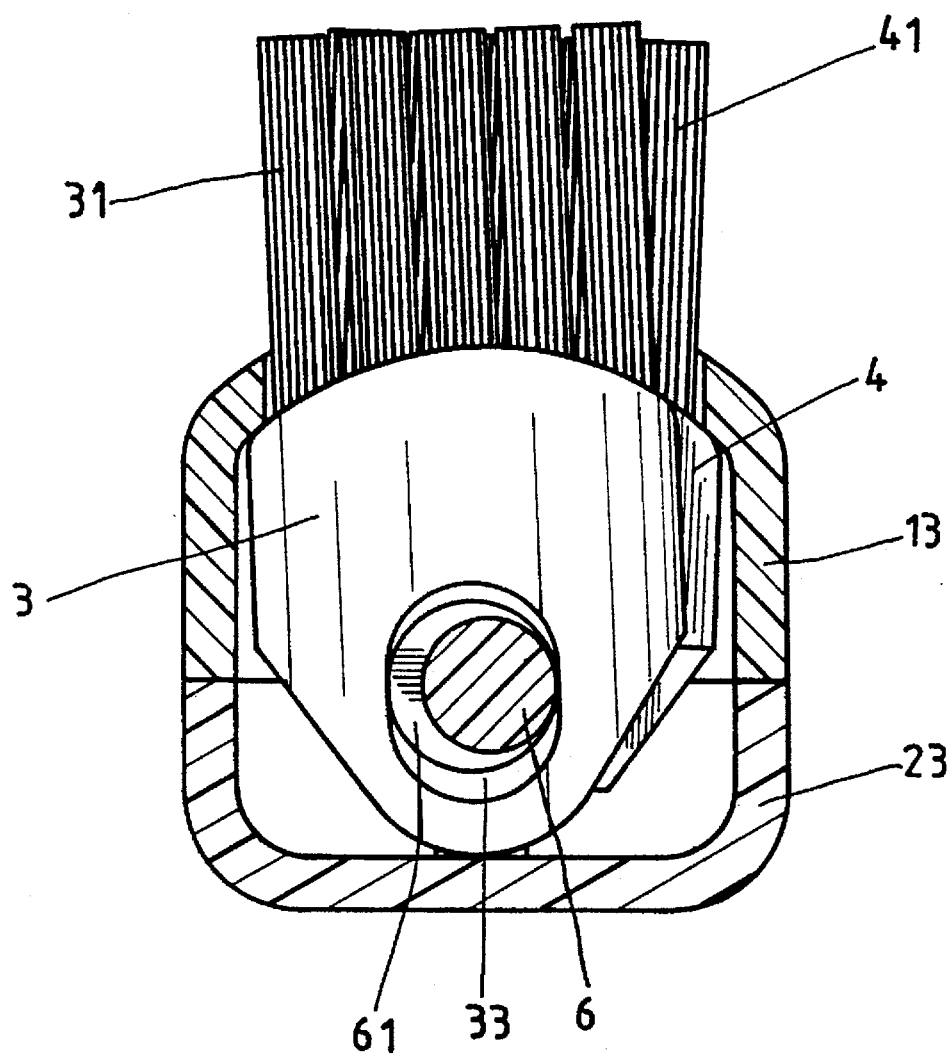
FIG. 4 is a cross-section view showing the operation of the head of the present invention.

In practicing, referring to FIG. 3 and FIG. 4, when the drive rod 6 is driven by a motor and a shaft (not shown in the figures) to rotate, the eccentric cam 61 drives the rear swing body 3 to rotate, and the swing bar 5 drives the front swing body 4 to rotate in an opposite direction. This allows the rear swing body 3 to eliminate the vibration effect, and to be in accord with the correct method of brushing teeth. On the other hand, while the drive rod 6 is rotating, the blade 62 can push the water and powder infiltrated therein from the gaps between the blocking rims 132 and 232 to the collar 63 at the rear end of the blade 62. The water and the powder will then be expelled out from slots 12 and 22 of the shell trunks 1 and 2 under the centrifugal effect.

I claim:

1. A brush head assembly of an electric toothbrush, said assembly adapted to be coupled to a motor driven shaft of said toothbrush, said assembly comprising:

an upper and lower elongated shell trunk coupled together, each shell trunk comprises a narrow first end portion and an enlarged second end portion having a width wider than said first end portion, each shell trunk forms a longitudinal recess therein at said first end portion such that together, the first end portions define a longitudinal pocket, each first end portion includes an elongated slot therethrough communicating with said pocket, each second end portion defines a head portion with a holding space therein, said head portion of said upper shell trunk has an opening therethrough which is surrounded by an extending curved blocking rim, said head portion of said lower shell trunk has two spaced concave grooves in a bottom side thereof and a pin extending from said bottom side;

adjacent first and second bristled swing bodies, each swing body having a curved top face, a curved end face, a bottom and a side, the sides of the swing bodies being in facing relationship and each side having a recess formed therein, each bottom of said swing body has a convex lug extending therefrom, said lugs being received, respectively, in said concave grooves, said second swing body has an oval blind hole in the curved end face;

an elongated swing bar, said bar is pivotally mounted to said pin and the opposite ends thereof are received into the recesses, respectively, of the swing bodies;

an elongated drive rod, said drive rod is received into the pocket for rotation therein, a first end of the drive rod has an eccentric cam thereon which is received into the oval blind hole in the second swing body, said drive rod has a helical blade extending along a surface thereof;

rotation of said drive rod causes rotation of said eccentric cam in said oval hole, such causes oscillation of the swing bodies in opposite directions due to pivoting of said swing bar, additionally, rotation of the drive rod causes rotation of the helical blade which acts to expel any water or debris present in said pocket out through the elongated slots.

* * * * *